US00PP29771P3

(12) United States Plant Patent
Danziger

(10) Patent No.: US PP29,771 P3
(45) Date of Patent: Oct. 23, 2018

(54) ***VERONICA* PLANT NAMED 'DVERSKYBLU'**

(50) Latin Name: *Veronica longifolia*
Varietal Denomination: DVERSKYBLU

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 24 days.

(21) Appl. No.: 15/530,408

(22) Filed: Jan. 9, 2017

(65) Prior Publication Data

US 2018/0199483 P1 Jul. 12, 2018

(51) Int. Cl.
*A01H 5/02* (2018.01)

(52) U.S. Cl.
USPC ..... Plt./251

(58) Field of Classification Search
USPC ..... Plt./251
See application file for complete search history.

*Primary Examiner* — Keith O. Robinson
(74) *Attorney, Agent, or Firm* — Cassandra Bright

(57) ABSTRACT

A new and distinct *Veronica* cultivar named 'DVERSKYBLU' is disclosed, characterized by naturally tall plants with long flowering spikes. Plants do not require vernalization.

2 Drawing Sheets

Figure 1:
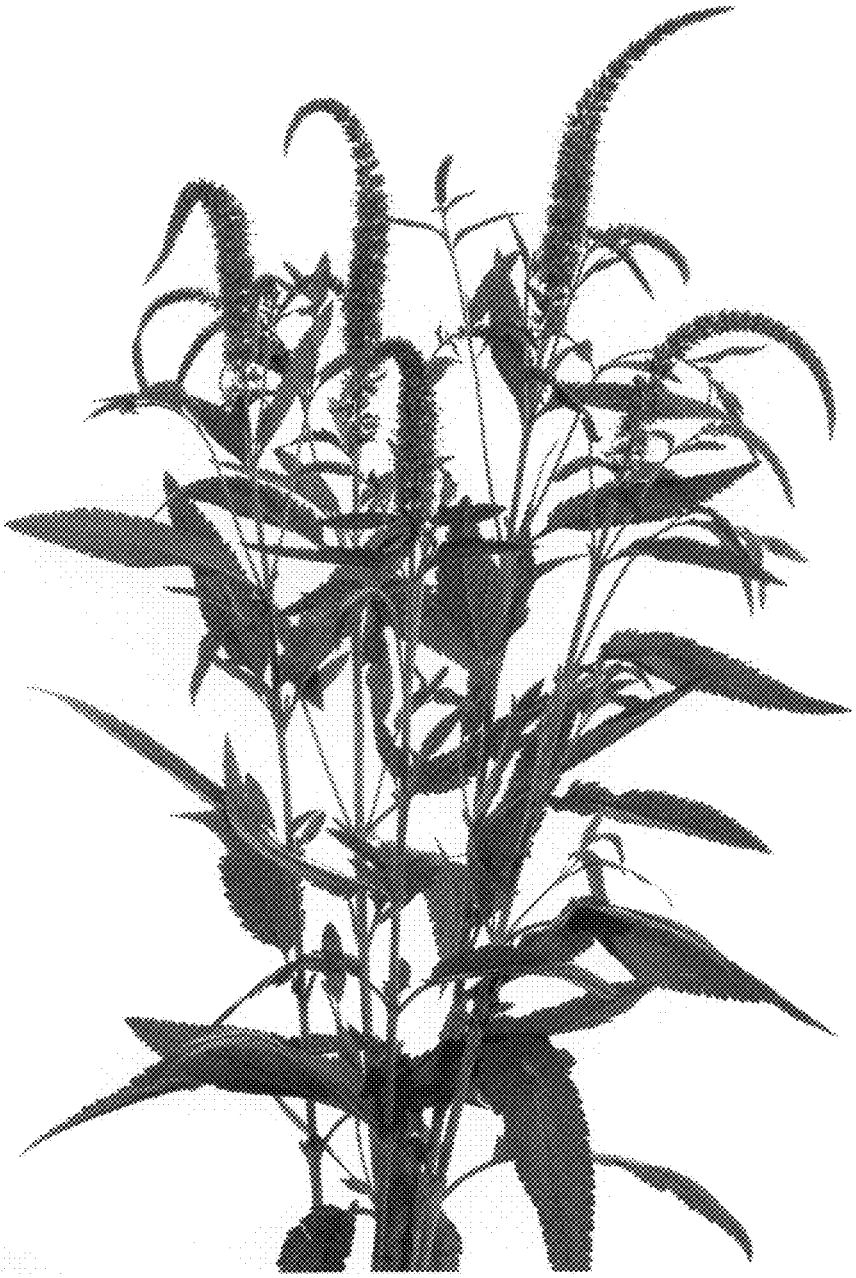

Latin name of the genus and species: *Veronica longifolia*.
Variety denomination: 'DVERSKYBLU'.

The new *Veronica* cultivar resulted as part of a planned breeding program by the inventor Gavriel Danziger. The objective of the breeding program was to develop new *Veronica* varieties with low vernalization requirements The new variety resulted from a controlled crossing of the seed parent, an unpatented, proprietary seedling referred to as 'VR-Z-2' with the pollen parent, an unpatented, proprietary seedling referred to as 'VR-Z-4'. The crossing was made at a research greenhouse in Israel during Spring of 2010. The new variety was first selected in Spring of 2011 by the inventor in a group of seedlings resulting from the 2010 crossing in a research greenhouse in Moshav Mishmar Hashiva, Israel.

Asexual reproduction of the new cultivar 'DVERSKYBLU' by vegetative cuttings was first performed at a greenhouse as well as outdoors in Moshav Mishmar Hashiva, Israel in 2011. Subsequent propagation by terminal vegetative cuttings has shown that the unique features of this cultivar are stable and reproduced true to type in several successive generations.

SUMMARY OF THE INVENTION

The cultivar 'DVERSKYBLU' has not observed under all possible environmental conditions. The phenotype may vary somewhat with variations in environment such as temperature, day length and light intensity, without however, any variance in genotype.

The following traits have been repeatedly observed and are determined to be the unique characteristics of 'DVERSKYBLU'. These characteristics in combination distinguish 'DVERSKYBLU' as a new and distinct *Veronica* cultivar:

1. Vernalization not required to induce flowering.
2. Long flowering spikes
3. Naturally tall plant.

COMPARISON TO THE PARENT VARIETY

Plants of the new cultivar are similar to plants of the seed parent, in most horticultural characteristics, however, plants of the new cultivar differ in the following;

1. The seed parent variety is shorter.
2. The seed parent variety requires some vernalization, the new variety requires no veranlization.
3. The seed parent flower color is lighter blue.

Plants of the new cultivar are similar to plants of the pollen parent, in most horticultural characteristics, however, plants of the new cultivar differ in the following;

1. Plants of the pollen parent require some vernalization, plants of the new variety require no veranlization.
2. Flowers of the pollen parent are pink, flowers of the new variety are blue.

COMPARISON TO COMMERCIAL VARIETIES

Plants of the new cultivar can be compared to the unpatented commercial variety *Veronica* 'Clea Diana'. These varieties are similar in most horticultural characteristics; however, the new cultivar differs in the following:

1. The new variety has a longer flower spike.
2. Plants of the new variety require less chilling hours for good performance.
3. Comparator variety is shorter.

Plants of the new cultivar can be compared to the unpatented commercial variety *Veronica* 'Skyler Pink'. These varieties arc similar in most horticultural characteristics; however, the new cultivar differs in the following:

1. Comparator flower color is pink, the new variety produces blue flowers.
2. Comparator variety produce more basal undergrowth.
3. Comparator variety begins flowering later than the 'DVERSKYBLU'.

BRIEF DESCRIPTION OF THE PHOTOGRAPHS

The accompanying photograph in FIG. 1 illustrates in full color a typical plant of 'DVERSKYBLU' grown in a greenhouse. Age of the plant photographed is approximately 10 to 12 weeks from a well rooted cutting.

Figure 2:
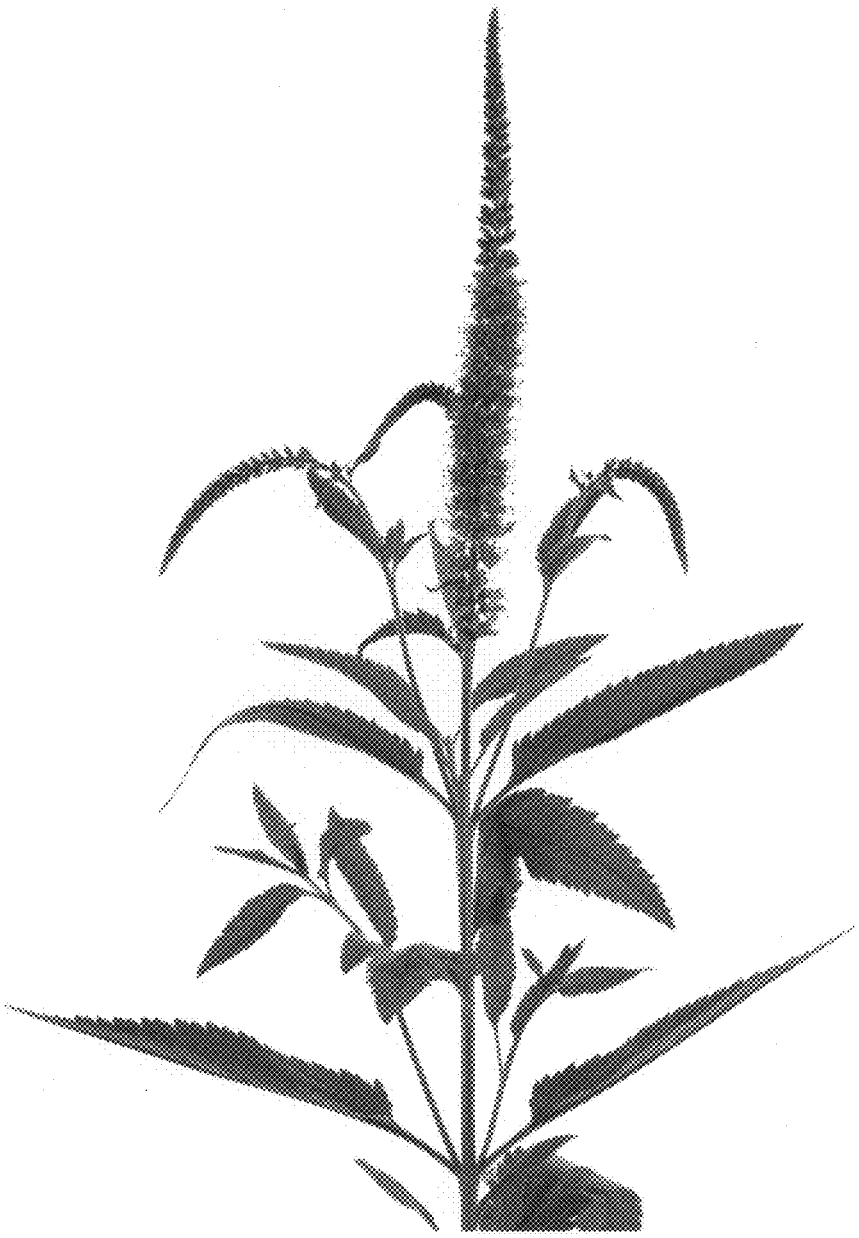

FIG. 2 illustrates a close up view of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurement describe 'DVERSKYBLU' plants at 10-12 weeks of age, grown in a tunnelhouse in Moshav Mishmar Harshiva, Israel between February and June. Plants were planted in the ground in February, given no veranlization treatment. The growing temperature ranged from about 15° C. to 20° C. during the day and about 5° C. to 10° C. night. General light conditions are bright, normal sunlight. Measurements and numerical values represent averages of typical plant types. No growth regulators were used.

Botanical classification: *Veronica longifolia.*

PROPAGATION

Time to initiate roots: About 18 days at approximately 20° C.

Root description: Vigorous rooting. Root system is larger than above ground plant. Fibrous. Tan to brown, not accurately measured with R.H.S. chart.

PLANT

Plant type: Perennial.
Growth habit: Upright.
Pot size of plant described: Plants in ground.
Height: About 60 to 70 cm.
Plant spread: About 20 cm.
Growth rate: Rapid, with no vernalization requirement.
Branching characteristics: Excellent basal branching.
Length of primary lateral branches: About 70 cm.
Diameter of lateral branches: Approximately 0.5-0.6 cm.
Texture of lateral branches: Smooth.
Internode length: 4-5 cm.
Strength of stem: Very strong.
Color of lateral branches: Near RHS Green 140B.
Aspect/angle of branches: Very upright, acute angle. Straight.
Number of leaves per lateral branch: Approximately 8 pairs (over 30 cm of stem) of primary leaves.

FOLIAGE

Leaf:
- *Arrangement.*—Opposite in pairs.
- *Length.*—Approximately 12-14 cm.
- *Average width.*—4 to 4.25 cm.
- *Shape of blade.*—Oval.
- *Apex.*—Extended acute.
- *Base.*—Rounded.
- *Margin.*—Serrate.
- *Texture of top surface.*—Smooth.
- *Texture of bottom surface.*—Protruding veins.
- *Appearance top surface.*—Matte.
- *Appearance bottom surface.*—Matte.
- *Leaf internode length.*—Approximately 4-5 cm.
- *Color.*—Young foliage upper side: Near RHS Green 137A. Young foliage under side: Near RHS Green 137C. Mature foliage upper side: Near RHS Green 135A. Mature foliage under side: Near RHS Green 137B.
- *Venation.*—Type: Pinnate. Venation color upper side: Indistinguishable from leaf blade. Venation color under side: Indistinguishable from leaf blade.

Petiole:
- *Petiole.*—Present.
- *Length.*—4 cm.
- *Diameter.*—0.2 cm.
- *Pubescence.*—None.
- *Color.*—Near RHS Green 137C.

FLOWER

Natural flowering season: Spring through Summer., best flowering occurring during March through June in Israel.
Days to flowering from rooted cutting: 60 days during the Spring season.
Flower longevity on plant: 12-14 days.
Persistent or self-cleaning: Self-cleaning.
Fragrance: None.

Bud:
- *Bud shape.*—Oblong.
- *Bud length.*—Approximately 0.7 cm. showing color.
- *Bud diameter.*—Approximately 0.25 cm.
- *Bud color.*—Near RHS137C.
- *Opening rate, from bud to fully open.*—2 days.

Inflorescence arrangement: Spike.
- *Inflorescence height.*—12-13 cm.
- *Inflorescence width.*—1.5-1.7 cm.
- *Quantity of flowers per inflorescence.*—50-70.
- *Typical quantity of inflorescence per plant.*—About 24.

Individual flower form: Campanulate.

Flower:
- *Diameter of entire flower.*—Approximately 0.6-0.7 cm.
- *Length of flower.*—Approximately 1-1.2 cm from tip of stamen to the base of the receptacle.

Petals/tepals:
- *Quantity.*—4.
- *Arrangement.*—
- *Length.*—0.5-0.6 cm.
- *Width.*—0.2-0.25 cm.
- *Shape.*—Orbicular.
- *Apex.*—Rounded.
- *Base.*—Squared.
- *Margin.*—Smooth.
- *Texture, upper and lower surfaces.*—Smooth.
- *Appearance upper and lower surfaces.*—Matte.
- *Color.*—When opening, upper surface: Near RHS Violet-Blue 93B. When opening, lower surface: Near RHS Violet-Blue 93B. Fully opened, upper surface: Near RHS Violet-Blue 93B. Fully opened, lower surface: Near RHS Violet-Blue 93B. Fading: Flowers fall off before fading.

Peduncle:
- *Peduncle length.*—Approximately 1.5 cm.
- *Peduncle diameter.*—Approximately 0.25 cm.
- *Angle.*—Straight upright.
- *Color.*—Near RHS Green 137D.
- *Peduncle texture.*—Slightly hairy.

Fragrance: None.
- *Strength.*—Strong.
- *Pedicel.*—None.

REPRODUCTIVE ORGANS

Androecium:

*Stamens*.—2.

*Anther shape*.—Oblong.

*Anther length*.—Approximately 0.1 cm.

*Anther color*.—Near RHS Violet-Blue 93A.

*Pollen quantity*.—Abundant.

Gynoecium:

*Pistil number*.—1.

*Pistil shape*.—Elongated and not branching.

*Pistil length*.—Approx. 1 cm.

*Pollen color*.—Yellow 4D.

*Style length*.—Approx. 0.095 cm.

*Style color*.—Near RHS 93D.

*Filament length*.—9-13 mm.

*Filament color*.—Near Violet-Blue 91D.

*Stigma shape*.—Round.

*Stigma color*.—Near RHS 93D.

*Ovary diameter*.—0.05 cm.

*Ovary color*.—Near RHS 137D.

OTHER CHARACTERISTICS

Seeds and fruits: Oblong seeds, approximately 0.5 mm, light brown, not accurately measured with an R.H.S. chart.

Disease/pest resistance: Tolerance for powdery mildew, probable pathogens include *Erysiphe, Leveillula, Microsphaera, Podosphaera* and *Spaerotheca*. Neither resistance nor susceptibility to other normal diseases and pest of *Veronica* have been observed. Typical well known diseases include: *Botrytis cineria*, and *Pythium*. The most common pest it white fly, potentially *Trialeurodes vaporariorum, Bemisia tabaci* or others.

Temperature tolerance: Typical range USDA zones 4 through 8.

What is claimed is:

1. A new and distinct *Veronica* plant named 'DVERSKY-BLU' as herein illustrated and described.

* * * * *